United States Patent [19]

Gordon

[11] Patent Number: 4,547,893
[45] Date of Patent: Oct. 15, 1985

[54] CONTINUOUS WAVE FAN BEAM TOMOGRAPHY SYSTEM HAVING A BEST-ESTIMATING FILTER

[75] Inventor: Bernard M. Gordon, Magnolia, Mass.

[73] Assignee: Analogic Corporation, Peabody, Mass.

[21] Appl. No.: 597,196

[22] Filed: Apr. 5, 1984

Related U.S. Application Data

[63] Continuation of Ser. No. 273,033, Jun. 12, 1981, abandoned.

[51] Int. Cl.⁴ .............................................. G03B 41/16
[52] U.S. Cl. ........................................ 378/19; 378/4
[58] Field of Search ..................................... 378/19, 4

[56] References Cited

U.S. PATENT DOCUMENTS 4,034,223  7/1977  Kowalski ............................ 378/901

*Primary Examiner*—Craig E. Church
*Attorney, Agent, or Firm*—David W. Gomes; Stephen G. Matzuk

[57] ABSTRACT

A continuous wave fan beam tomographic system having continuous x-ray absorption values sampled at a sampling rate and means to provide a best-estimate of the x-ray absorption values at discrete points in time. The means to provide a best-estimate includes a continuous filter having a frequency range defined by the geometry of the mechanical system. Errors due to the statistical variation in photon emissions of the x-ray source are thereby minimized and the effective signal-to-noise ratio of signals is enhanced, which in turn allows a significant reduction in radiation dosage.

5 Claims, 8 Drawing Figures

CONTINUOUS WAVE FAN BEAM TOMOGRAPHY SYSTEM HAVING A BEST-ESTIMATING FILTER

This application is a continuation of application Ser. No. 273,033, filed June 12, 1981, now abandoned.

FIELD OF THE INVENTION

This invention relates to tomography and more particularly to continuous wave fan beam tomography systems which measure a continuous radiation beam at a plurality of radiation detectors, wherein the source and the detectors move continuously and circumferentially about the subject examined.

BACKGROUND OF THE INVENTION

Computer aided tomography systems derive images by placing the subject between a source and one or more radiation sensors, wherein a source of radiation and radiation sensors move together in one or more rotational or lateral axes. The computer aided tomography systems produce the image by indirect means. Specifically, a multiplicity of x-ray readings are taken of the subject which in themselves do not directly characterize the elements within the subject as known and readable to the human observer. The computer then interprets the multiplicity of x-ray readings taken together in a particular manner in which a readable image is created to define the subject of interest. A subgroup of tomography systems of present interest is known as continuous wave fan beam tomography systems. The term "continuous wave fan beam" specifies the radiation source to be continually emitting radiation in a beam pattern resembling a sector of a circle. As part of this type of system, there are typically several hundred radiation sensors in the path of the fan beam on the opposite side of the subject to receive the x-ray radiation as attenuated along defined path lines through the subject. The sensors form an arcuate segment of sufficient length to intercept the entire radiation beam transmitted along a path through and absorbed by the subject from the radiation source and generate individual output signals. In prior fan beam tomography systems simultaneous acquisition of all x-ray readings for each gantry position are believed to be the most preferred manner in which to provide the necessary mathematical basis for tomographic image (re)construction. The individual radiation sensor output signals are therefore (in prior systems) each initially processed by individual resettable integrators, known collectively as the "integrate-and-dump" technique, which are then sampled and stored by subsequent system elements. According to the continuous wave fan beam tomography systems and included techniques of the prior art, it is believed that the best estimate of the radiation attenuation along each defined path can be derived from the individual outputs of integrate-and-dump circuits which are designed to collect as much detector output signals, and therefore x-ray radiation signals, as possible.

Another aspect of prior art, relating to computer-aided continuous wave fan beam tomography systems has been the great expense of the required associated auxiliary circuitry, in addition to the several hundred precision resettable integrators. In general, auxiliary transfer circuitry has been required for each input channel to rapidly receive, upon a transfer command, the accumulated integration values, allowing the aforesaid input integrators to be rapidly reset at the end of an integration period and be allowed to continue to integrate during the next integration time interval.

A universal goal in tomography systems is to reduce the radiation dosage. The dosage requirements are generally defined by the detector sensitivity to x-ray radiation, the radiation detector geometry and the subsequent signal processing apparatus. In the prior art, it is assumed that collecting as much radiation signal as possible (with a resettable integrator for each radiation detector) was the best way of minimizing the radiation dosage. However, in spite of system improvements according to prior art teachings, the dosage required still remains relatively high, thus limiting the number of examinations any one subject may undergo.

SUMMARY OF THE INVENTION

The present invention filters the detector output signals from moving x-ray detectors in a continuous wave fan beam tomography system by known filters, described by determined parameters, having output signals sampled at a sampling rate. The tomographic image is accurately formed from radiation values derived, at discrete points in time from the filter output signals, thus eliminating the need to simultaneously sample all detector outputs at the discrete points in time, as in prior art systems. The gantry position moves continuously wherein specific gantry positions are related to the discrete points in time. The filter output signals are sequentially sampled at a sampling rate which typically differs from the discrete points in time. The derived radiation values are each a best-estimate value at specific gantry positions according to the sequentially sampled filter output signals. The accuracy of the best-estimated radiation value is enhanced by removing error signals from the filter output signals according to the filter design. The filters are optimized according to parameters which include filter bandwidth, filter transient response, filter phase response, system geometry limitations, subsequent computer reconstruction method and system cost. In so doing, the filters minimize error signals included in the detector output signals which, in turn, improves the estimate of the x-ray absorption at the discrete points in time. For instance, the inventive concept recognizes that the maximum frequency of the signal derived by the continuous wave tomography systems is fundamentally limited by the source of the radiation, the size of the target to be detected, the cross-sectional area of the radiation detector and the geometry and motion of these components relative to each other. Furthermore, it is recognized that photon randomness can be expressed as noise having a noise bandwidth far in excess of the remaining tomography system bandwidth. The present invention improves the signal quality significantly by processing the detector signals with a temporally continuous filter to limit the noise, whose output is sufficiently sampled prior to conversion for subsequent processing.

More specifically, according to the present invention, a substantial amplitude of error signal arising from the radiation source is removed by filtering the detector signals with a low-pass filter having a cutoff at a frequency below the sampling rate. The mechanical system, including the detectors, produces a signal which is essentially a convolution of the target with the detector cross-section. The resulting time varying signal has its associated frequency components which have a related bandwidth. One embodiment of the invention provides a low-pass filter which extends only to the maximum useable frequency of the above-mentioned bandwidth. The sampling rate is determined according to the maximum useable frequency. The maximum useable frequency is selected according to an objective or a subjective analysis of a Fourier transform of the time varying signal in view of the above-mentioned criteria. The present invention thereby provides increased signal-to-noise and resolution of the signals which are used to compute tomographic images. The improvement is sufficient to allow an image to be reconstructed from the data obtained with a reduced source radiation level. This, in turn, provides a lower subject dosage and increased availability of the tomographic aided diagnosis to the public.

Additionally, the system according to the present invention includes continuous filtering before sampling and eliminates the need for individual storage elements (for each sensor) in tomography systems, which significantly decreases overall system cost.

Briefly, the continuous wave fan beam tomography system according to the present invention includes a continuous wave radiation source and a plurality of radiation detectors positioned in opposition to the source about the subject to be examined. A gantry retains and moves the radiation source and the radiation detectors about a center of rotation located within said subject. The radiation source provides a fan beam (generally known within the art as uniform radiation in a fan shape in a first plane and having a small width and substantially no divergence in a second plane, and a fan angle at the first plane of sufficient magnitude to illuminate the entire subject cross-section). The detectors are located behind the subject to form an arcuate segment sufficiently long to fully intercept the radiation transmitted through the subject. Each detector provides a detector output signal relating the radiation received. The detector output signal is then filtered by a plurality of detector filters having an input to receive the detector output signals optimized to produce a continuous filter output signal relative to each detector output signal which provides a determinable best-estimate of the total x-ray radiation absorption along a determined path through the subject when the filter output signal is sampled at a sampling rate by subsequent elements of a continuous wave fan beam tomography system including a processing computer. An image is reconstructed according to a best-estimated x-ray value at discrete points in time which, in view of the sequential nature of the filter output sampling, are skewed in time from the sampling rate, or have a different periodicity.

The sampling periods occur at a sampling rate, which also determines a practical limit to the bandwidth of the detector filters. The sampling rate is limited to a frequency corresponding to a maximum useable frequency of the detector output signal. The maximum useable frequency of the detector output signals is determined according to the largest and smallest object or target to be resolved, the size and location of each detector and the mechanical system movement relative to the subject. The source of radiation, the objects to be resolved and detector cross-section are convolved in time to produce a time varying signal, the Fourier transform of which describe a group of frequency domain signals having an uppermost frequency domain signal. The maximum useable frequency is related according to a subjective or a determined known objective analysis of the uppermost frequency domain signal. It is according to the present invention that signals outside of the above-specified bandwidth are, in general, error signals, noise or other unwanted signals and are to be minimized. The resulting signal may be processed in a processing computer to form best-estimate signals derived from the sampled filter output signals. The best-estimate signals are formed for discrete point in time (which typically differ from the sampling rate), where the discrete points in time relate to specific gantry positions. The processing computer forms a tomographic image in a variety of known manners; the image is then subsequently displayed by appropriate display means.

BRIEF DESCRIPTION OF THE DRAWING

These and other features of the present invention are more fully described in the following detailed description and in the accompanying drawing in which.

DETAILED DESCRIPTION OF THE INVENTION

Figure 1:
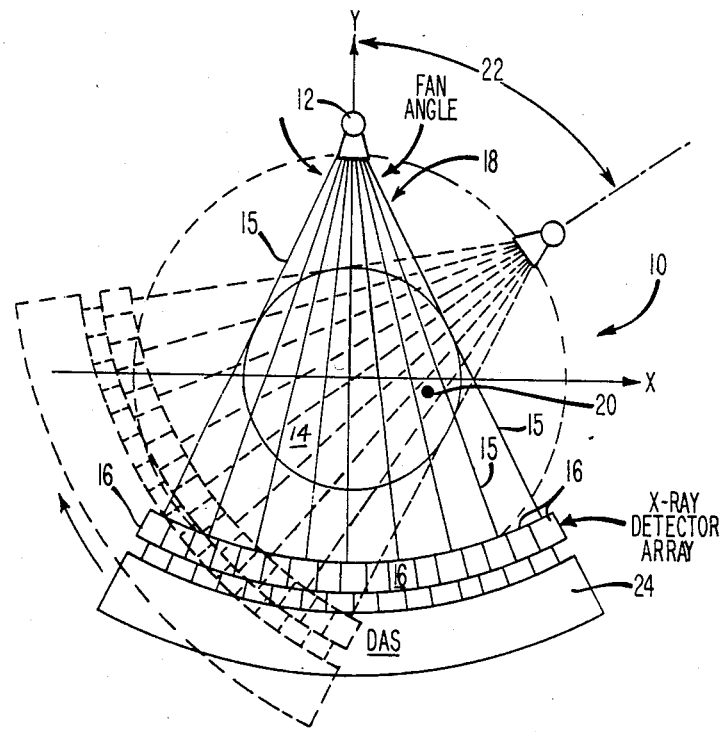
FIG. 1 is a schematic representation of the mechanical geometry of a typical continuous wave fan beam tomography system.

Turning now to the drawing and in particular FIG. 1, a generalized schematic view of the geometry of a continuous wave fan beam tomography system is shown in a mechanical configuration generally known as a gantry 10 containing an x-ray source 12 which emits a continuous broad x-ray beam for the transmission through the subject 14 to an array of x-ray detectors 16, each having a detector cross-sectional area. The emitted radiation fan beam 18 diverges from source 12 as the emission travels towards the plurality of detectors 16, (diverging over a fan angle in a sector pattern through the subject 14 in a first plane perpendicular to the subject, where the sector pattern has a relatively narrow width substantially without divergence in a second plane extending perpendicular to the first plane along the axis of the subject). Of interest is the detection and imaging of particular targets within the subject 14, those targets being exemplified by a single target 20. The source 12 and the detector array 16 move together about the subject 14 through a rotation angle and direction labeled 22; the desired information is typically produced by a rotation through an angle 22 of 360°, while the source 12 emits a continuous fan beam of radiation 18. The plurality of detectors each provide a continuous signal relating the reception of x-ray photons from the source 12 through the subject 14 as the assembly is continuously moved through the rotation angle 22. The signals from the detector array are each directly related to the volume of photons received, and therefore it is inversely proportional to the absorption of the subject 14 through each line 15 traveled by the x-rays from the source 12.

The signals produced by the detectors are conditioned by a data acquisition system 24. The data acquisition system 24 contains a plurality of channels, one for each detector output signal and provides an output signal for additional data acquisition logic such as signal multiplexers and digitizers, not shown. Thereafter, the signal is processed by a general purpose or a specialized processing computer system 28 in a predetermined manner to provide a reconstructed image of a transaxial view. A complete fan beam tomography system, described in greater detail in U.S. Pat. No. 4,135,247, is hereby incorporated by reference. The above-mentioned subsequent signal processing may be provided according to the above-mentioned patent or by other ways currently known.

According to FIG. 1, it can be seen that the presence of a target 20 is detected by a shadow which it casts by absorbing the energy of the beam 18 as seen by one of the detectors 16. The position of the target and its shape is deduced from its level of absorption according to the line integral over each path 15 as well as its motion relative to the source 12 and the detectors 16. The reconstruction of the target 20 may be provided according to known techniques.

The method and apparatus according to the present invention concerns the formation of a best-estimate of the absorption for each path 15 through the subject 14 at discrete points in time for a given set of values for the rotation angle 22 of the source 12 and detector array 16. The best-estimates at the discrete points in time are interpolated, synthesized, or otherwise derived from sequentially sampled detector signals in an image processor, which reconstructs a tomographic image. It is therefore essential that the sampled detector signals allow such best-estimated absorption values to be derived accurately.

Figure 2:
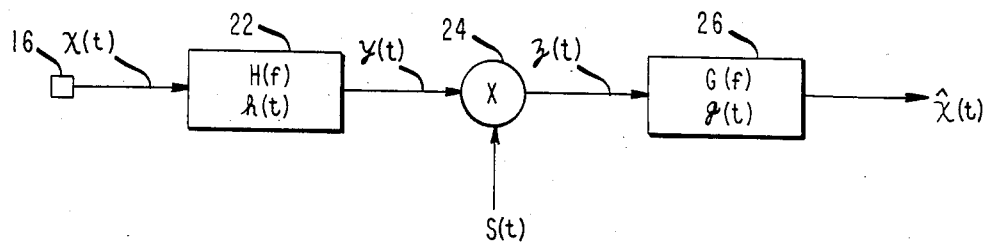
FIG. 2 is a block diagram of a generalized sampling and reconstruction subsystem of the present invention.
Figure 2A:
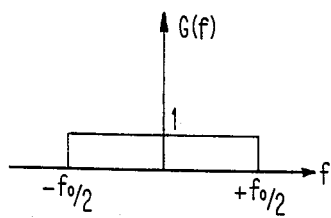
FIG. 2A is the transfer characteristic of one element of the subsystem of FIG. 2.
Figure 6:
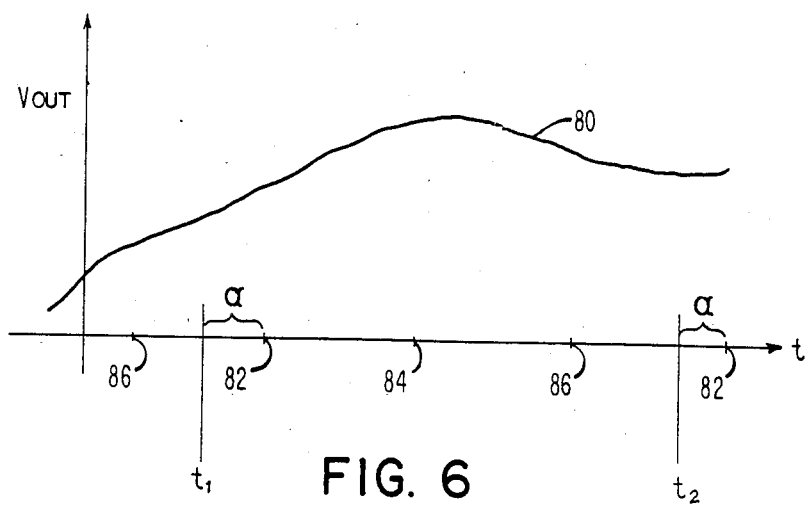
FIG. 6 is a typical filter output signal of the circuit of FIG. 4.

The system pre-processing functions can be generalized as shown in FIG. 2, wherein each detector 16 produces a output signal x(t) received by a functional block 23 with a generalized transfer function H(f) or time domain response h(t). The block 23 produces an output y(t) which is periodically and instantaneously sampled by sampling block 25 according to sampling signal s(t) to produce a sampled signal z(t). More specifically, the sampling signal s(t) is defined in a generally known form:

$$s(t) = \sum_{K=-\infty}^{\infty} \frac{1}{T} U_o(t - Kt - \alpha), \quad T = \frac{1}{f_o} \quad (1)$$

where $U_o$ is an impulse function, $\alpha$ is a statistical phase constant (see FIG. 6) and $f_o$ is the sampling frequency. The samples of y(t) form z(t) as $$z(t) = \sum_{K=-\infty}^{\infty} y(Kt + \alpha)U_o(t - KT - \alpha) \quad (2)$$

where the set of values {y(Kt+α)} are the sample values. The reconstructed output x(t) is given by $$\hat{x}(t) = \sum_{K=-\infty}^{\infty} y(Kt + \alpha)g[t - Kt - \alpha] \quad (3)$$

where functional block 26 has the transfer characteristic shown by FIG. 2A, or that of an ideal low pass filter.

An error ε(t) can be defined in the sampling and reconstruction process. The detector 16 output x(t) is assumed to have a spectral density $S_x(f)$ and an α uniformly distributed over the time interval [0,T], allowing the definitions:

$$\epsilon(t) \stackrel{\Delta}{=} \hat{x}(t) - x(t), \quad (4)$$

$$S_x(f) \stackrel{\Delta}{=} S_L(f) + S_H(f) \quad (5)$$

where $S_L(f) = S_x(f), \quad |f| < \frac{f_o}{2} = 0$, elsewhere $\quad (6A)$ and $S_H(f) = 0, \quad |f| < \frac{f_o}{2} \quad (6B)$ $= S_x(f), \quad |f| \geq \frac{f_o}{2}$ The statistical average means-square error $\epsilon^2(t)$ function:

$$\overline{\epsilon^2(t)} = \int_{-\frac{f_o}{2}}^{+\frac{f_o}{2}} |1 - H(f)|^2 S_L(f) df + \int_{|f| > \frac{f_o}{2}} |1 + H(f)|^2 S_H(f) df \quad (7)$$

which, when reduced, provides the least sampling and reconstruction error, is minimized when:

$$H(f) = 1, \quad |f| < \frac{f_o}{2} \quad (8)$$

$$= 0, \quad |f| \geq \frac{f_o}{2}$$

to produce an error which is:

$$\overline{\epsilon^2(t)} = \int_{|f| > \frac{f_o}{2}} S_H(f) df \quad (9)$$

which includes all signal power of x(t) outside of the reconstruction region, earlier defined as being between $[-f_o/2, f_o/2]$.

Thus, according to one embodiment of the invention incorporating linear filtering for all discrete points in time (α not limited to a particular value), the best reconstruction of x(t) resides within the bandwidth $[-f_o/2, f_o/2]$ for a given sample rate $f_o = 1/T$. The best linear estimator x(t) is therefore obtained with H(f) of 23 comprising that of an ideal low pass filter, shown in FIG. 3 at 40, which passes all signals at a frequency equal to or below the filter cutoff frequency, and rejects all signals at a frequency greater than the cutoff frequency, and an error given by the high-frequency power of x(t) as defined by equation (9). However, if x(t) has no high-frequency power, $S_H(f)=0$, then $\epsilon^2(t)=0$ for optimum H(f).

Figure 2B:
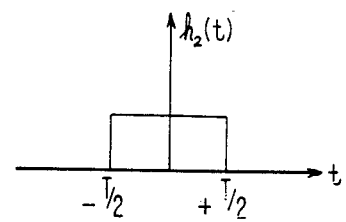
FIG. 2B is the time response of a prior art integrate-and-dump circuit in the context of the subsystem of FIG. 2.
Figure 3:
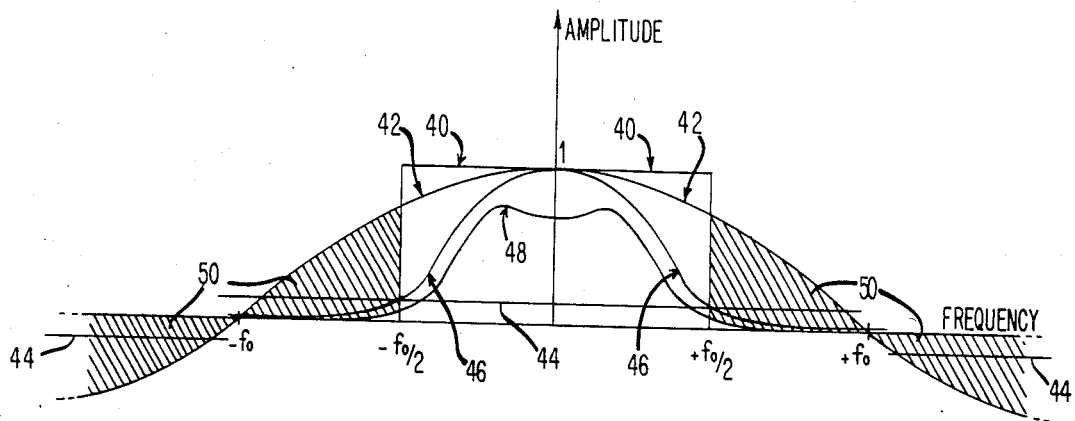
FIG. 3 is a graph of the signals of interest in the frequency domain.

When h(t) is $h_2(t)$ as shown in FIG. 2B for a typical prior art integrate-and-dump response over time period T, the function block 22 transfer response is $$H_2(f) = \text{Sin } \pi f T / \pi f T \quad (10)$$

shown as curve 42 in FIG. 3, and can be compared in FIG. 3 as wave 42 with the optimum filter response 40 to reveal error signals indicated by shaded areas 50 which exist whenever $S_H \neq 0$. Therefore, to minimize extraneous signal energy, such as photon noise power discussed below, the optimum filter is an idealized low-pass filter. In other words, any signals passed by G(f), shown by FIG. 2A, and H(f) above the sampling frequency (above $S_L$) will result in the addition of unrecoverable error. The sampling rate $f_o$ is selected to be at least two times greater than the highest useful frequency component in x(t) from the sensor 16 according to the Nyquist criteria. The highest useful frequency component may be objectively or subjectively selected (considering the above-mentioned system parameters) according to the overall shape of the frequency domain characteristics of the detector or target signals.

The overall shape of the frequency domain characteristics of target signals is described according to the Fourier transform of the respective time varying signal, which is the convolution of the cross-section with the target cross-section as the two are moved respective to each other during the rotational scan period of the source and the detectors relative to the patient. A typical frequency domain representation of the signals present in the tomography system of interest is shown in FIG. 3. For illustration, hypothetical broadband signal derived from a long target with sharp irregularities in the time domain is shown in the frequency domain by curve 48 on FIG. 3. Most generally, the low frequency limit is defined by the maximum duration of the absorption or shadow cast by the object during the rotation, e.g., a cross-section of the skull at a nearly tangential detection sight wil show a continuous absorption during the revolution of the gantry, resulting in a DC component, thereby defining the low frequency requirement. The upper frequency requirement is the limit imposed by sharpness or the rapidity of the variations of the time varying convolution signal.

The major source of error in the reconstructed signals arise from the inherent uncertainty of the source emissions; that is, the regularity with which the x-rays are produced by a source of radiation and that the electronic system noise is generally relatively minor. Although the photon noise is broadband, the signals derived by the mechanical system appearing at the detector outputs have a limited bandwidth in relation to the target to be imaged within the subject. The present invention improves the usefulness or accuracy of reconstructed signals by restricting the bandwidth of those electrical signals passed according to the maximum bandwidth as defined by the target and the mechanical geometry of the tomography system as described above and sacrifices the remaining signal from the detector outputs as unwanted noise.

It is shown in FIG. 3, according to the present invention, that the performance may be enhanced significantly by providing a filter circuit adjusted to pass primarily the convolution signal 48 produced at the detector output, and minimize the contribution of the photon noise 44 beyond the maximum useful frequency of the convolution signal. A typical filter of that description is shown by curve 46, having the characteristic of a three-pole Butterworth filter with a 3 dB point of approximately 380 hertz when the sample period is one millisecond.

Figure 4:
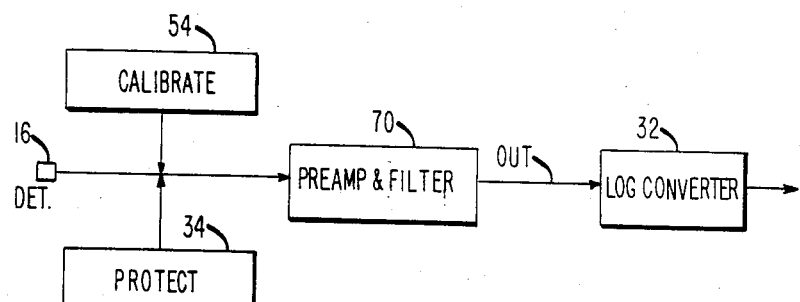
FIG. 4 is a block diagram of a single channel of the continuous filter according to one embodiment of the present invention.

An embodiment of one channel of the data acquisition system, according to the filter of the present invention includes a detector amplifier in the amplifier-filter 70, shown in FIG. 4. The remaining calibration 54 and protection 34 circuitry of each channel may be retained as in the prior art or other circuitry modifications may be made according to known methods and apparatus. The specification of the filter 3 dB point, as well as its other characteristics, e.g. Butterworth, Tchebycheff, Elliptical or other filter types, are made at the designer's discretion in a known manner according to the desired phase, frequency and time characteristics of the data acquisition system, the mechanical system, subsequent processing of the image signals into a completed tomographic picture and total system cost. The careful design and selection of the filter characteristics in relation to the desired criteria, mentioned above, will result in a signal of improved signal-to-noise ratio.

Figure 5:
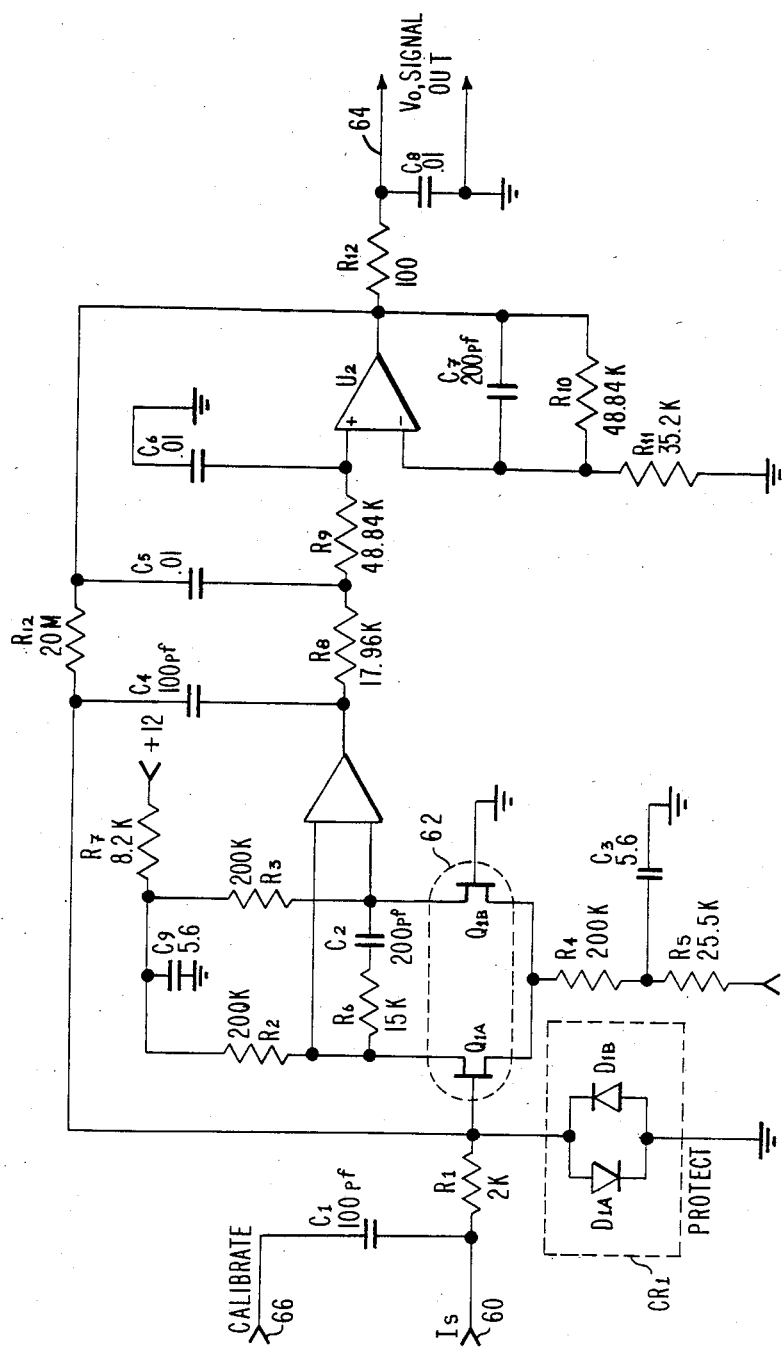
FIG. 5 is a schematic diagram of one embodiment of the continuous filter according to the present invention.

One embodiment of the continuous filter according to the present invention is shown in detail in FIG. 5. The detector provides a current output, Is to be received by input 60 through resistor $R_1$ into the gate of a differential J-FET pair $Q_{1A}$, $Q_{1B}$ typically contained within a common enclosure 62 to provide closer matched operations of the J-FET pair over a temperature range. The protective circuit (34 of FIG. 1 and FIG. 5) is implemented by $CR_1$ containing back-to-back diodes $D_{1A}$ and $D_{1B}$ across the $Q_{1A}$ gate to ground. The J-FET pair is biased from $-12$ volts by $R_4$ and $R_5$ bypassed with $C_3$ to ground. The $Q_{1B}$ gate input is connected to ground establishing a zero volt operating point of the circuit of FIG. 6. The drain load resistors of $Q_{1A}$ and $Q_{1B}$ and $R_2$ and $R_3$, respectively, are connected to $+12$ volts through a common resistor $R_7$ bypassed by $C_9$. The drains of J-FET pair $Q_{1A}$ and $Q_{1B}$ are received by the non-inverting and inverting inputs of operational amplifier $U_1$, typically a TL062, commercially available. Resistor $R_6$ and capacitor $C_2$ form a compensating network for $U_1$ connected across the inputs of $U_1$. The J-FET pair function as a high impedance input stage for $U_1$; the J-FET pair $Q_{1A}$ and $Q_{1B}$ and operational amplifier $U_1$ operate in concert to form a high input impedance operational amplifier. A filter network is formed comprising resistors $R_8$, $R_9$, $R_{10}$, $R_{11}$ and $R_{12}$, capacitors $C_4$, $C_5$, $C_6$ and $C_7$, operational amplifier $U_2$ (typically a 741, commercially available) and previously mentioned operational amplifier $U_1$ in conjunction with J-FET pair. The filter output Vo appears at 64, which includes the operational amplifier $U_2$ output as filtered by network $R_{13}$ in combination with $C_8$ to work in combination with preceding circuit components to effect a determined overall filter response. The characteristics of the filter of FIG. 4 are derived according to known engineering methods to provide a low-pass Butterworth with a 3 dB point of 380 Hz and an overall gain below 380 Hz of $V_o/I_s = 2 \times 10^7$. A calibrate signal of predetermined amplitude generated by calibration means 54 of FIG. 4 is provided at 66 into capacitor $C_1$; when the calibrate signal is not provided, the calibrate input 66 is grounded.

The present invention permits the filter output signal to be continuously sampled at a rate desired, typically at the rate greater than that specified by the Nyquist criteria according to the highest frequency desired, e.g., if the highest frequency is about 380 hertz, a sampling period of 1 millisecond will suffice. In addition, higher sample rates are permissible as desired where the filter 70 output, after being processed by analog-to-digital converter 32, is shown by signal 80 in FIG. 6, with sampling points occurring at points 82, 84 and 86 between time intervals $t_1$ and $t_2$.

Each of the filters as described above provide as an output, in response to respective input signal from respective detectors in continuous wave fan beam tomography systems, a continuous signal providing a best-estimate of the radiation absorption along the path between said radiation source and the respective detector at discrete points in time. The discrete points in time are skewed in time, or have different periodicities, relative to said sampling period for at least some of the filter signals.

The subsequent processing, digitization and display of the signal from each channel of the data acquisition system is provided by means and according to methods known in the art. Additional improvements in the image reconstruction in the attached processing computer system 28 is anticipated due to the increased information provided by the increased sample rate beyond the minimum Nyquist rate, as well as the decreased error signal from photon randomness in the filter output signal. These enhancements may be made in a manner known in the art.

The construction of best-estimate reconstructed signals by continuous filtering for detector signals having more complex spectral distributions and in systems utilizing sampling rates at other than twice the highest useable frequency are within the scope of this invention.

It is also within the scope of the present invention to sufficiently over-sample the filter output signal so that a part of the above-described filter or additional filter or correction processes and apparatus may be included as part of and within the above-mentioned processing computer. For instance, a filter may be formed within the processing computer according to methods and apparatus known in digital filtering to add several additional poles, or to provide phase correction characteristics according to the characteristics of the discrete filter embodiment described above.

These and other embodiments according to the present invention made by those skilled in the art are within the scope of the invention, which is not to be limited to what has been described except as defined by the appended claims.

What is claimed is:

1. A method of forming a tomographic image comprising the steps of:
    exposing a subject to a beam of x-ray photons from an x-ray source along a path;
    continuously moving said path through a subject;
    receiving said beam of x-ray photons substantially continuously including a first set of discrete points in time, on an array of detectors disposed opposite said x-ray source;
    filtering the output of each said detector by filter means allowing a maximum useable frequency to pass and rejecting error signals containing a noise signal therein above said maximum useable frequency, the maximum useable frequency being defined by the internal structure of the subject and by the relative motion of said beam of x-ray photons;
    instantaneously sampling the output of each said filter means at a respective second set of discrete points in time which are substantially different from said first set of discrete points; and
    reconstructing an image from the sampled output including deriving a signal for each said filter means for each of said discrete points in time of said first set, said derived signals being representative of the x-ray photons received by the respective detectors at said first set of discrete points in time.

2. The method of claim 1 wherein said step of instantaneously sampling includes defining a sampling interval for said second set of discrete points in time according to said maximum useable frequency and making said sampling interval no greater than one-half of the reciprocal of said maximum useable frequency, generally known as the Nyquist criteria.

3. A continuous wave fan beam tomography system to resolve targets in a subject comprising:
    a radiation source providing x-ray photons in a continuous fan beam;
    a plurality of detectors each providing a signal output according to the x-ray photons received, said detectors being disposed in an array arranged to receive said x-ray photons substantially continuously including a first set of discrete points in time and in the plane of said fan beam;
    a gantry to retain and move said radiation source and said plurality of detectors at a gantry rate about a center of rotation located within said subject;
    a plurality of filters each receiving a detector output signal and providing a continuous output signal;
    means for instantaneous sampling said filter continuous output signals and for providing a periodic sequence of instantaneous samples for each said detector at a respective second set of discrete points in time which are substantially different from said first set of discrete points in time;
    each said filter having a cutoff above which signal frequencies are substantially rejected, said cutoff being determined to exclude a noise signal at frequencies above a maximum useable frequency, wherein the maximum useable frequency is a function of the internal structure of the object and of the relative motion of the source of x-ray photons;
    processing means for reconstructing an image according to said periodic sequences of instantaneous samples said processing means including means for providing a derived signal for each of said filter output signals for each of said discrete points in time of said first set, said derived signals being representative of the x-ray photons received by the respective detectors at said first set of discrete points in time.

4. A continuous wave tomography system comprising:
    a radiation source providing x-ray photons in a continuous wave beam;
    a plurality of detectors disposed in an array and arranged to receive said x-ray photons, substantially continuously including a first set of discrete points in time, in a plane within said x-ray beam, each of said detectors providing an output signal according to the x-ray photons received;
    a gantry for retaining and moving said radiation source and said plurality of detectors at a gantry rate;
    a plurality of filters for selecting useful signals and rejecting noise signals each receiving said output signal of a respective one of said detectors;
    sampling means coupled to said plurality of filters for instantaneously sampling said filtered output signals and for providing a periodic sequence of instantaneous samples for each said detector at a respective second set of discrete points in time which are substantially different from said first set of discrete points; and means coupled to said sampling means for providing a derived signal for each of said detectors for each of said discrete points in time of said first set, each said derived signal being representative of the photons received by the respective said detector at said first set of discrete points in time.

5. Apparatus of claim 1 wherein:

each said filter has a maximum useable frequency above which signal frequencies are substantially rejected and said maximum useable frequency is determined accordingly to an object to be resolved and the gantry movement in association with the size and location of each said detector; and further wherein said second set of discrete points in time are separated by a sampling interval determined in response to said maximum useable frequency.

* * * * *